US012656360B2

(12) United States Patent
Rudorfer et al.

(10) Patent No.: US 12,656,360 B2
(45) Date of Patent: Jun. 16, 2026

(54) METHODS AND APPARATUS FOR PREDICTING AND PREVENTING FAILURE OF IN VITRO DIAGNOSTIC INSTRUMENTS

(71) Applicant: Siemens Healthcare Diagnostics Inc., Tarrytown, NY (US)

(72) Inventors: Arnold Rudorfer, Princeton, NJ (US); Steven Magowan, Elkton, MD (US); Govindraj Peesapati, Monmouth Junction, NJ (US); Robert Kachelries, West Chester, PA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 18/636,098

(22) Filed: Apr. 15, 2024

(65) Prior Publication Data

US 2024/0255533 A1 Aug. 1, 2024

Related U.S. Application Data

(63) Continuation of application No. 16/316,057, filed as application No. PCT/US2017/042564 on Jul. 18, 2017, now abandoned.

(60) Provisional application No. 62/366,360, filed on Jul. 25, 2016.

(51) Int. Cl.
*G01N 35/00* (2006.01)
*G16H 40/40* (2018.01)

(52) U.S. Cl.
CPC . *G01N 35/00623* (2013.01); *G01N 35/00871* (2013.01); *G16H 40/40* (2018.01)

(58) Field of Classification Search
CPC ....... G01N 35/00623; G01N 35/00871; G05B 2219/32287; G05B 2219/34477; G05B 2219/45169; G05B 23/0243; G16H 40/40
See application file for complete search history.

(56) References Cited

U.S. PATENT DOCUMENTS

| | | | |
|---|---|---|---|
| 2002/0077795 A1* | 6/2002 | Woods ..................... | G01N 3/10 703/6 |
| 2002/0128728 A1 | 9/2002 | Murakami et al. | |
| 2005/0007249 A1 | 1/2005 | Eryurek et al. | |

(Continued)

FOREIGN PATENT DOCUMENTS

| | | |
|---|---|---|
| WO | 2015023443 A1 | 2/2015 |
| WO | 2015179370 A1 | 11/2015 |

*Primary Examiner* — Michael J Dalbo

(57) ABSTRACT

Methods of predicting failures of in vitro diagnostic instruments include monitoring, with one or more monitoring devices associated with one or more components of the in vitro diagnostic instrument, one or more condition-based maintenance (CBM) parameters of the in vitro diagnostic instrument, providing the one or more condition-based maintenance parameters to a local database, transmitting condition-based maintenance data to a remote service location, storing the condition-based maintenance data at the remote service location, analyzing the condition-based maintenance data according to a failure prediction engine including failure prediction criteria, and performing an action based on predefined deviation from the failure prediction criteria. Apparatus configured to carry out the methods are provided, as are other aspects.

14 Claims, 4 Drawing Sheets

(56)                    References Cited

U.S. PATENT DOCUMENTS

| | | | |
|---|---|---|---|
| 2007/0067678 A1* | 3/2007 | Hosek | G05B 23/0235 |
| | | | 714/25 |
| 2008/0040152 A1 | 2/2008 | Man et al. | |
| 2008/0143515 A1 | 6/2008 | Wood et al. | |
| 2008/0312783 A1 | 12/2008 | Mansouri et al. | |
| 2009/0177427 A1 | 7/2009 | Bauer et al. | |
| 2010/0185711 A1* | 7/2010 | Subramaniam | G16H 20/10 |
| | | | 709/203 |
| 2012/0249158 A1* | 10/2012 | Schmelzeisen-Redeker | |
| | | | A61B 5/1486 |
| | | | 324/537 |
| 2013/0139616 A1* | 6/2013 | Yamamoto | G16H 40/40 |
| | | | 73/863.01 |
| 2014/0005505 A1* | 1/2014 | Peyser | A61B 5/1459 |
| | | | 600/347 |
| 2014/0067327 A1 | 3/2014 | Jiang et al. | |
| 2014/0176345 A1* | 6/2014 | Schiff | G08B 23/00 |
| | | | 340/870.16 |
| 2014/0266790 A1* | 9/2014 | Al-Ali | G06F 11/30 |
| | | | 340/870.09 |
| 2015/0260742 A1* | 9/2015 | Nakajima | G01N 35/00613 |
| | | | 422/63 |
| 2015/0273691 A1 | 10/2015 | Pollack | |
| 2016/0132375 A1* | 5/2016 | Jacobs | G16H 40/40 |
| | | | 714/47.2 |

* cited by examiner

METHODS AND APPARATUS FOR PREDICTING AND PREVENTING FAILURE OF IN VITRO DIAGNOSTIC INSTRUMENTS

RELATED APPLICATIONS

This is a continuation of U.S. patent application Ser. No. 16/316,057, filed Jan. 8, 2019, which is a 371 of PCT/US2017/042564, filed Jul. 18, 2017, which claims priority to U.S. Provisional Patent Application No. 62/366,360, filed Jul. 25, 2016, each of the disclosures of which are hereby incorporated by reference in their entireties herein.

FIELD

The present disclosure relates to methods and apparatus adapted to predict failures in instruments.

BACKGROUND

In medical testing and processing, automated apparatus such as in vitro diagnostic instruments may include the use of robotics and are used to test and/or process biological liquids (otherwise referred to herein as "specimens"). Such automated apparatus is complex and from time-to-time may experience failures (e.g., malfunctions). Certain types of recurring malfunctions are relatively easy to diagnose and the apparatus itselve may generate an "error code," which will lead the user to a set of instructions that provide a solution to rectify the malfunction. However, these types of solutions may be problematic.

Accordingly, methods and apparatus that may improve upon malfunction solutions in such in vitro diagnostic instruments are sought after.

SUMMARY

In one method embodiment, a method of predicting failures of an in vitro diagnostic instrument is provided. The method includes monitoring, via one or more monitoring devices associated with one or more components of the in vitro diagnostic instrument, one or more condition-based maintenance parameters of the in vitro diagnostic instrument; providing the one or more condition-based maintenance parameters of the in vitro diagnostic instrument to a local database; transmitting condition-based maintenance data to a remote server; storing the condition-based maintenance data at the remote server; analyzing the condition-based maintenance data according to a failure prediction engine including failure prediction criteria; and performing an action based on predefined deviation from the failure prediction criteria.

In an apparatus embodiment, an in vitro diagnostic instrument maintenance apparatus is provided. The apparatus includes one or more monitoring devices configured to monitor condition-based parameters of one or more instrument components; a local server coupled to the one or more monitoring devices, the local server including: an instrument check module configured to test functionality of the one or more instrument components, and obtain the condition-based parameters of the one or more instrument components; a local database configured to contain a compilation of the condition-based parameters; a remote server configured to communicate with the local server and configured to receive and store the condition-based parameters in a condition-based parameter database, the remote server including: a failure prediction engine, and a failure rules model.

In another embodiment, an in vitro diagnostic instrument maintenance apparatus is provided. The in vitro diagnostic instrument maintenance apparatus includes monitoring devices configured to monitor condition-based parameters of instrument components of an in vitro diagnostic instrument; a local workstation server of the in vitro diagnostic instrument coupled to the monitoring devices, the local workstation server including: an instrument check module configured to test functionality of the instrument components, and obtain the condition-based parameters of the instrument components; a local database configured to contain a compilation of the condition-based parameters; a remote server configured to communicate with the local workstation server and configured to receive and store the condition-based parameters in a condition-based parameter database, the remote server including: a failure prediction engine, and a failure rules model.

Still other aspects, features, and advantages of the present disclosure may be readily apparent from the following detailed description illustrating a number of example embodiments. The present invention may also be capable of different embodiments, and its several details may be modified in various respects, all without departing from the scope of the present disclosure. Accordingly, the disclosure is to cover all modifications, equivalents, and alternatives falling within the scope of the disclosure as defined in the claims.

DETAILED DESCRIPTION

Failures in automated medical testing and processing equipment (e.g., in vitro diagnostic instruments) are typically diagnosed after they occur, such as by the operator receiving an equipment-generated error code indicating that a malfunction has occurred and providing instructions on how to rectify the identified malfunction. This after-the-fact, reactionary approach, although adequate for malfunction diagnosis in the in vitro diagnostic instruments, may result in excessive repair downtime, and possibly extra labor costs due to overtime for unnecessarily-urgent repairs.

In one or more embodiments, an in vitro diagnostic instrument maintenance apparatus and method helps to detect upcoming or impending failures. The method and apparatus measures performance of one or more specific condition-based maintenance parameters (hereinafter "CBM parameters") in order to make predictions about impending malfunctions.

Knowing the performance of one or more specific CBM parameters, a failure prediction engine may compare the one or more measured CBM parameters against a pattern library of "normal" parameters that are indicative of normal behavior. If the measured value of the CBM parameter over time is deviating from the "normal" as identified by a CBM failure prediction engine, appropriate actions can be undertaken to address the deviation. The identification of a deviating CBM parameter may be indicative of deterioration (e.g., wear or impending failure) of a component (motor, heating unit, carousel, pump, valve, aspiration/dispense system, interfaces between sub-systems, processors, power supplies, or the like). When a CBM parameter deviation of a predefined magnitude (e.g., slope above a predetermined magnitude) is measured, the component can be fixed by a customer service engineer before the instrument stops working.

Such in vitro diagnostic instrument maintenance apparatus and methods may provide one or more benefits and/or advantages, such as: 1) reduced instrument down-time by knowing upfront what the root-cause and what needs to be fixed, 2) reduced mean time to repair by having the right set of components (spare parts) available (in advance) to replace the defective ones, 3) ability to schedule repairs at opportune times, 4) increased first time repair rates, and/or 5) reduction in service spare parts by knowing upfront which components are most likely to fail.

In view of the foregoing, one or more embodiments of the disclosure provides methods and apparatus configured and operable to rapidly identify and notify an operator of an impending malfunction of an in vitro diagnostic instrument.

These and other aspects and features of embodiments of the disclosure will be described with reference to FIGS. 1-4 herein.

Figure 1:
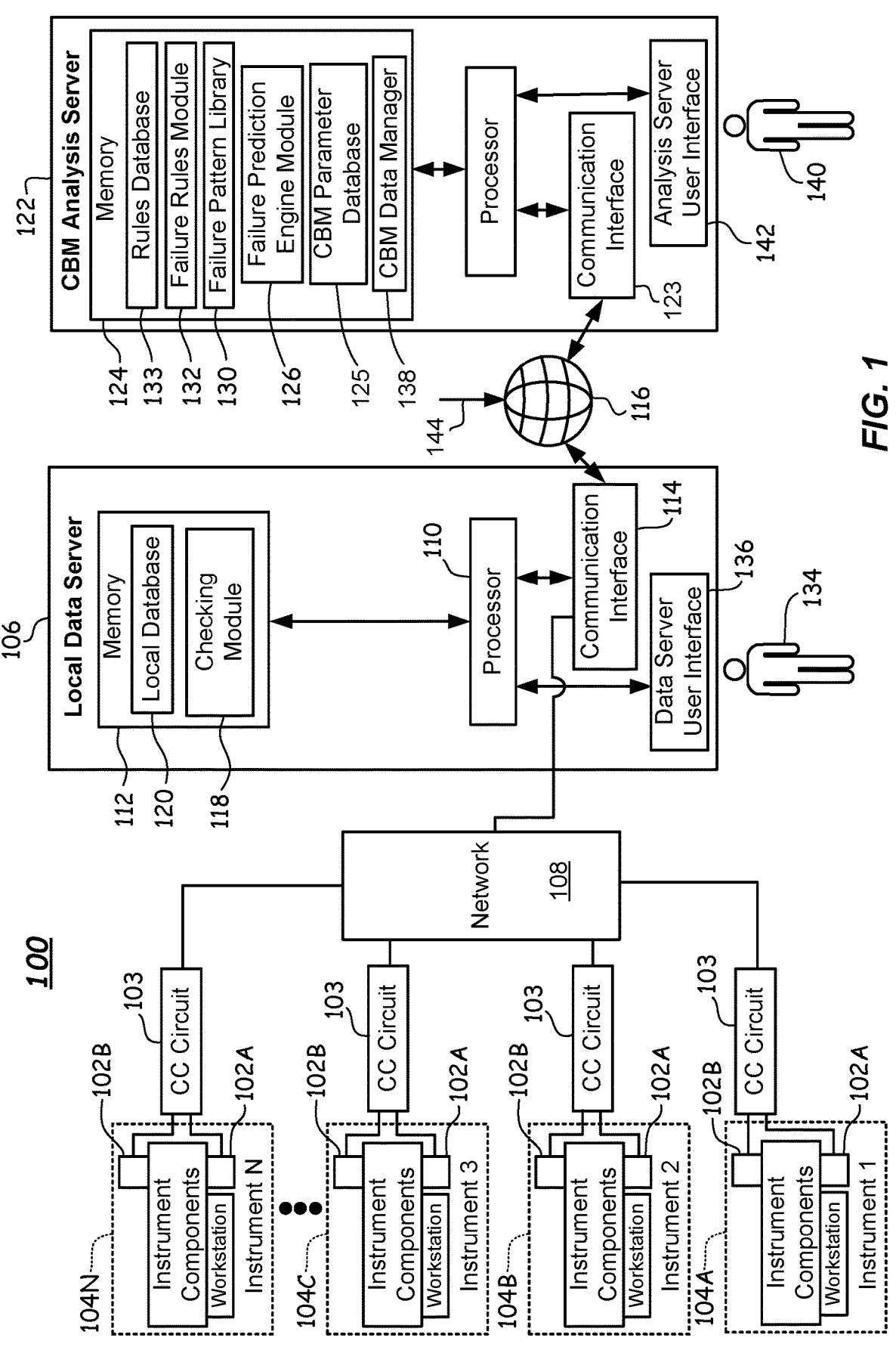
FIG. 1 illustrates a schematic diagram of an in vitro diagnostic instrument maintenance apparatus for multiple instruments at a location according to one or more embodiments.
Figure 2:
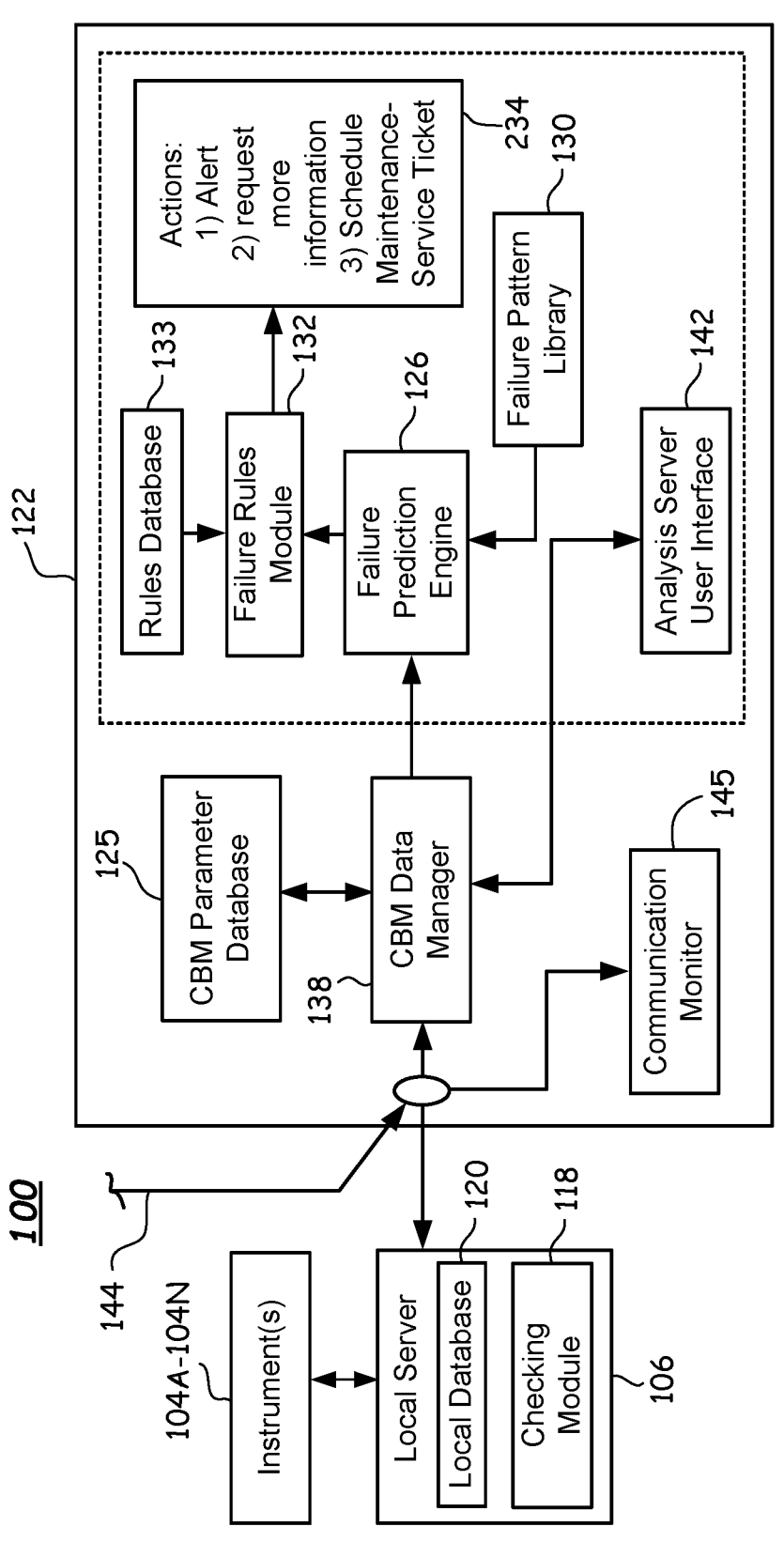
FIG. 2 illustrates a schematic functional diagram of an in vitro diagnostic instrument maintenance apparatus according to one or more embodiments.

In accordance with one or more apparatus embodiments, referring to FIGS. 1 and 2, an in vitro instrument maintenance apparatus 100 is shown and described. The in vitro instrument maintenance apparatus 100 includes one or more monitoring devices 102A, 102B configured to monitor condition-based parameters of one or more instrument components of one or more instruments 104A-104N. One or more than one instrument 104-104N may be monitored. The one or more instruments 104A-104N may comprise one or more testing and/or processing apparatus, such as clinical chemistry testing apparatus, immuno-assay testing apparatus, vessel mover, sample handler, and/or the like. One or more than one of the components of the testing and/or processing apparatus of one or more of the instruments 104A-104N may be monitored. The components of the instruments 104A-104N being monitored may be one or more motors, pumps, probes, aspiration/dispense systems, valves, reservoirs, lines, moving components, and/or the like.

Monitoring by the monitoring devices 102A, 102B may be by way of sensors or current and/or voltage sensors/taps on electrical circuits, or other suitable devices. Sensors may be used, for example, to monitor time, distance, position, strain, drift, load, resistance (friction or electrical), speed, acceleration, temperature, # of cycles, component level, light presence, intensity, and/or gradients, pressure and/or vacuum levels, fluid level, flow, leaks, or fluid presence or absence, fluid constituent concentration or condition, bubbles, vibration, noise, capacitance, contamination, contact, closure, state, proximity, or the like of various subcomponents. Condition of pumps, motors, or other electrical components may be monitored by current and/or voltage taps on electrical circuits that are coupled to the motors, pumps, and/or other electrical components. Backlash or other types of degradation may be monitored. In other embodiments, software-related CBM parameters may be monitored, such as bar code reader cycles (or reads and/or failures), component connectivity, processor crashes, restarts, CPU utilization, memory usage, or the like. Derivatives and/or integrals, or other manipulations of measured values of any of the above may be obtained and monitored.

The in vitro instrument maintenance apparatus 100 may include a local data server 106 coupled to the one or more monitoring devices 102A, 102B. For example, the coupling may be by way of a network 108, such as a suitable wired or wireless network. Each of the monitoring devices 102A, 102B may include a conditioning/communication circuit (e.g., CC circuit 103) that is operable to processes the signal from the monitoring device 102A, 102B and provide it in proper form for communication to the local data server 106 through the network 108. Network 108 may be a local area network (LAN), wireless local area network (WLAN), power line communication (PLC) network, or the like. Other suitable networks may be used.

The local data server 106 may be any suitable computer device including a processor 110, memory 112, and communication interface 114. Communication interface 114 may include any suitable device or devices enabling communication with the network 108 and the internet 116, such as Ethernet adapter, and a router and/or modem, or the like.

Local data server 106 may include a checking module 118 (otherwise referred to as an instrument check/device check component), which may be configured to: test functionality of the one or more components of one or more devices included in the instruments 104A-104N. For example, the one or more devices may be one or more analyzers, a sample handler, vessel mover, pre-analytic module (e.g., centrifuge), post-analytic module, decapper, recapper, or the like of an in vitro diagnostic instrument 104A-104N. Functionality may be tested by any suitable means, such as reading digital inputs and/or outputs, reading analog inputs, and motor status signals, testing connectivity of motors and/or heaters, and/or verifying that signals are within a normal operating range therefor. In some embodiments, checking module 118 may obtain the condition-based parameters of the one or more instrument components such as a pressure signal value, an acceleration value, a motor anomaly such as backlash or slop, a velocity value (linear or rotational), a displacement value (linear or rotational), a current value, a voltage value, a power value, a state, a light (e.g., photometer) reading, a level reading, a noise reading, transducer or sensor noise level, a valve condition reading, a fluid condition reading (e.g., pH), and/or the like. Derivatives, integrals, or other manipulations of the above may be used as the end CBM parameter that is monitored.

Data on functionality and condition-based parameters of the one or more instrument components may be stored in memory 112 in a local database 120. Data may include time stamps as well as absolute values. Local database 120 may be configured to contain a compilation of the condition-based parameters for each instrument 104A-104N being thus monitored. The compilation may include the data sampled over time, and may include maximum value, minimum value, mean value, and/or standard deviation. In the depicted embodiment, the local database 120 may receive condition-based parameters from multiple instruments 104A-104N. Sampling may be taken at any suitable interval, such as every minute, day, week, upon startup, or any other time period.

The apparatus 100 may include a remote server, such as a CBM analysis server 122 shown, that may be configured to communicate with the local data server 106. Communication may be via communication interface 123 communicating with local data server 106 through the internet 116, for example. Remote server (e.g., CBM analysis server 122), which may be at a different facility than local data server 106, may receive and store data on the CBM parameters and functionality data from the local data server 106 in memory 124, such as in a condition-based maintenance (CBM) parameter database 125. The data may include the previously-mentioned raw data, time stamps, and may include maximum, minimum, mean, and/or standard deviation data of the various instrument components. Other suitable related or associated data may be included.

The CBM analysis server 122 may also include a failure prediction engine module 126, and a failure rules model 132 configured as software or a combination of hardware and software. The failure prediction engine module 126 uses the data on CBM parameters from the one or more instruments 104A-104N to generate predictions of impending failures of components thereof.

For example, data over time may be collected for condition-based parameters such as pump backlash of multiple pumps of an aliquotter, IMT Probe, reagent arm location, sample probe pressure and/or location, and/or other components. The collected condition-based parameters may be compared against failure patterns and/or normal patterns stored in a failure pattern library 130. If the collected condition-based parameters over time are determined to be dissimilar enough (from a normal pattern) or similar enough (as compared to a failure pattern) from a corresponding pattern stored in the failure pattern library 130, then the failure rules module 132 may be triggered. The degree of dissimilarity may be determined by exceeding one or more thresholds or any other pattern recognition method. In some embodiments, a deviation from normal of a suitable magnitude above one or more threshold magnitudes is noted as denoting a failure pattern, wherein normal patterns may be stored in the failure pattern library 130. A solver may also provide some indication of the confidence level in the failure prediction, based on the degree of similarity or difference. In other embodiments, failure patterns may be stored in the failure pattern library 130 and failure may be determined based on the degree of likeness of the measured to the stored failure pattern. Likeness may be determined by being above certain thresholds or within pre-established threshold bands. Other suitable means for determining the similarity or difference, as the case may be, may involve curve fitting and goodness of fit, multi- or linear regression analysis, nonlinear regression analysis, Mahanobolis distance analysis, decision trees, or the like.

Based on the rule for the deviation of that type, a rule is collected from the rules database 133 and fired and a suitable action is launched by the failure rules module 132. For example, the actions may be as provided in block 234 of FIG. 2. In one example, the action may be an alert that provides a warning to the local operator 134 through the data server user interface 136. The warning may be provided through a visual warning (e.g., displayed on a visual display monitor) to the local operator 134 and/or a remote operator 140 that a component of an instrument 104A-104N is about to malfunction. An audible warning may also be initiated. Optionally or additionally, a service call (e.g., service ticket) may be initiated to an instrument manufacture or servicer, wherein a service technician is sent to the location of the instrument 104A-104N to repair the component that has been flagged as being subject to an impending failure on the instrument 104A-104N. Suitable spare parts may be taken with the service technician based upon knowledge of the impending failure provided by failure rules module 132.

A CBM data manager 138 may be configured as software or a combination of software and hardware and may facilitate exchange of data between the failure prediction engine module 126 and the CBM Parameter database 125. Further, CBM data manager 138 may initiate pull of CBM parameters from the local database 120 through communication interface 123 as commanded via input from the remote operator 140 through analysis server user interface 142.

In other embodiments, the CBM data manager 138 may initiate pull of the CBM parameter data from the local database 120 at preprogrammed intervals, such as hourly, daily, or other suitable intervals. In other embodiments, the checking module 118 may be preprogrammed to push the data to the CBM analysis server 122 via the communication interface 114 at preprogrammed intervals, such as hourly, daily, or other suitable intervals. In other embodiments, the local operator 134 may initiate, via suitable commands, a push of the CBM data to the CBM analysis server 122 via the communication interface 114.

Other instruments (not shown) coupled to other local servers (not shown) may also provide CBM parameters and functionality data through the internet 116 (as indicated by arrow 144) to communication interface 123 such that failure prediction thereof may also occur in the manner described herein. A communication monitor 145 may be included to identify the identity of the local data server (e.g., local data server 106) and respond as to the completeness of respective communications and data transmission therefrom.

Figure 3:
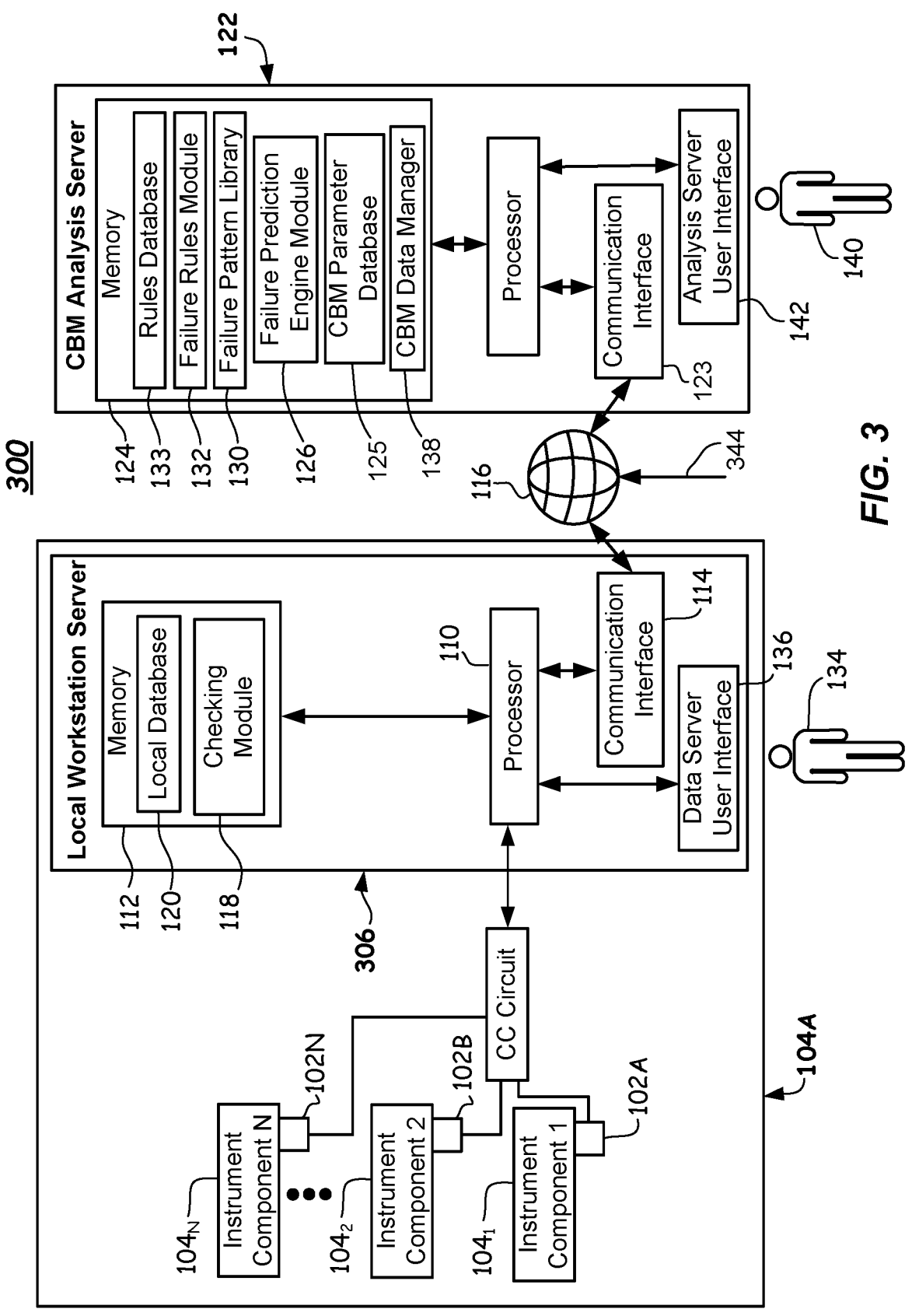
FIG. 3 illustrates a schematic diagram of an in vitro diagnostic instrument maintenance apparatus for a single instrument at a location according to one or more embodiments.
Figure 4:
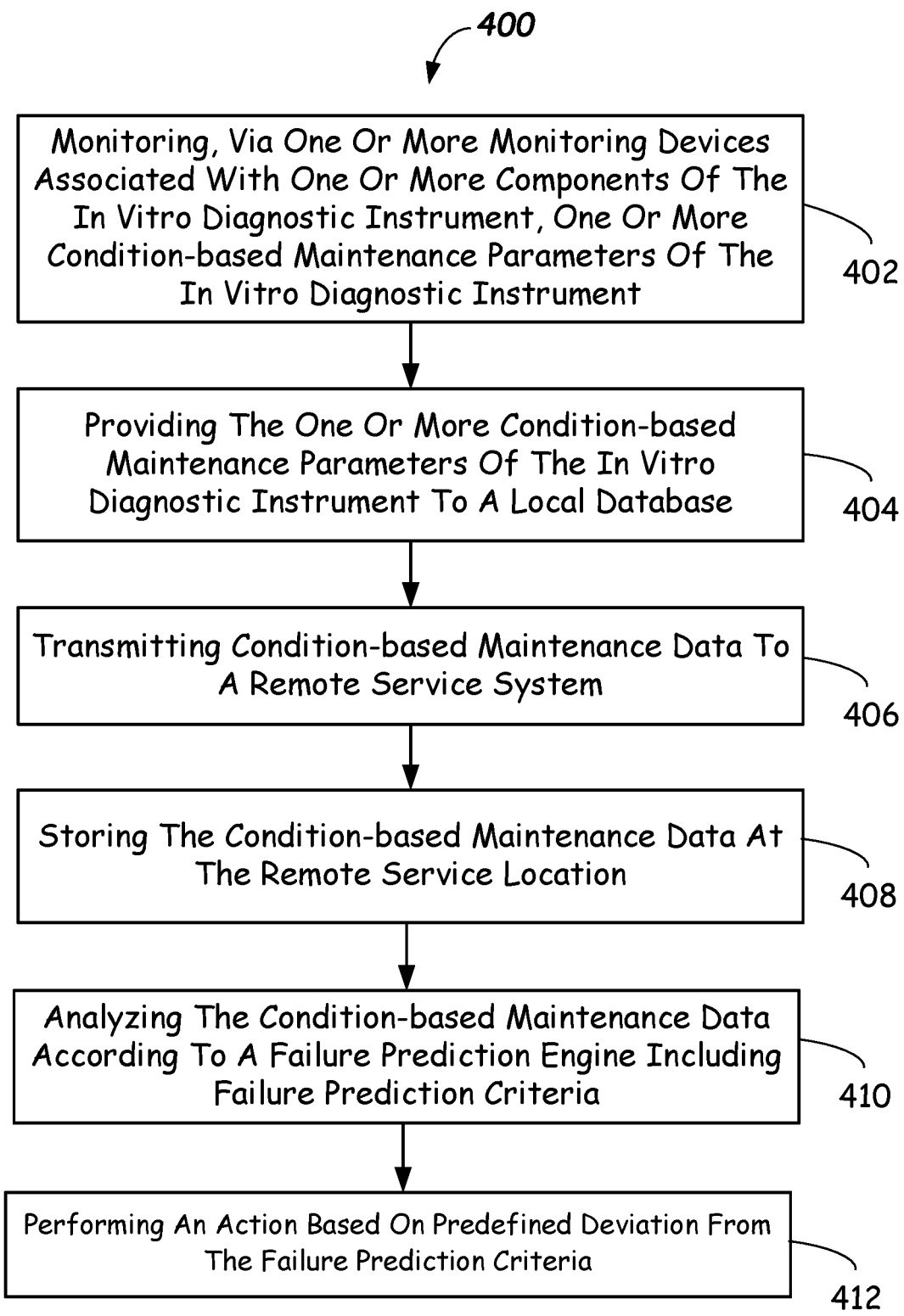
FIG. 4 illustrates a flowchart of a method of predicting failures of an in vitro diagnostic instrument according one or more embodiments to embodiments.

In accordance with another embodiment of the disclosure, an in vitro diagnostic instrument maintenance apparatus 300 is shown and described with reference to FIG. 3. The in vitro diagnostic instrument maintenance apparatus 300 includes monitoring devices 102A-102N configured to monitor condition-based parameters of instrument components $104_1$-$104_N$ of an in vitro diagnostic instrument 104A. Monitoring devices 102A-102N may be as discussed herein above. Multiple components of the in vitro diagnostic instrument 104A may be monitored.

The in vitro diagnostic instrument 104A may include a local workstation server 306 of the in vitro diagnostic instrument 104A coupled to the monitoring devices 102A-102N. The local workstation server 306 is configured to operate the components $104_1$-$104_N$ and one or more devices of the in vitro diagnostic instrument 104A. The local workstation server 306 may include, as previously described, a checking module 118 configured to: test functionality of the instrument components $104_1$-$104_N$, and obtain the condition-based parameters of the instrument components $104_1$-$104_N$, which are stored in memory 112. The local workstation server 306 may include a local database 120 configured to contain a compilation of the condition-based parameters.

The in vitro diagnostic instrument maintenance apparatus 300 may include a remote server (e.g., a CBM analysis server 122) as previously described. CBM analysis server 122 may be configured to communicate with the local server (e.g., local workstation server 306) and configured to receive and store the condition-based parameters in the CBM parameter database 125, wherein the remote server (e.g., a CBM analysis server 122) includes a failure prediction engine module 126, and a failure rules module 132, which function to predict impending failure and issue corrective actions. CBM parameters and data from other in vitro diagnostic instruments (not shown) may also be provided to the remote server (e.g., CBM Analysis server 122) through communication through the internet 116 as indicated by arrow 344.

In accordance with another embodiment of the disclosure, a method 400 of predicting failures of an in vitro diagnostic instrument (e.g., in vitro diagnostic instrument 104A-104N)

is provided. The method 400 includes, in 402, monitoring, via one or more monitoring devices (e.g., 102A-102N) associated with one or more components (e.g., components 104₁-104ₙ) of the in vitro diagnostic instrument, one or more condition-based maintenance parameters of the in vitro diagnostic instrument. Data on functionality of the (e.g., instrument components 104₁-104ₙ) may also be monitored. In 404, the method includes providing the one or more condition-based maintenance parameters of the in vitro diagnostic instrument to a local database (e.g., to local database 120). Any suitable sampling routine may be used. In 406, the condition-based maintenance data is transmitted to a remote server (e.g., CBM analysis server 122). Transmission may be automatic at any suitable interval or initiated by local operator 134 or remote operator 140. In 408, the method 400 includes storing the condition-based maintenance data at the remote server (e.g., in CBM parameter database 125), such as in a CBM parameter database 125 in memory 124.

The method 400 further includes, in 410, analyzing the condition-based maintenance data according to a failure prediction engine (e.g., failure prediction engine module 126) including failure prediction criteria. The failure prediction criteria may be a pattern wherein a pattern of the condition-based maintenance data is compared against known (previously collected) patterns in the failure pattern library 130 for that component. Any suitable method for comparison may be used, such as threshold-based comparisons, wherein if a preselected threshold is exceeded, then a failure may be predicted to occur. The method 400 further includes, in 412, performing an action based on predefined deviation from the failure prediction criteria. For example, if the deviation is above a defined threshold amount then an action may be undertaken; otherwise, the CBM analysis server 122 continues to monitor the component. Actions may include alerts (e.g., warnings, request for additional information, such as input from the local operator 134, requests for further functionality data or condition-based maintenance data by either the local operator 134 or remote operator 140, or scheduling of maintenance including possibly ordering replacement parts for worn or parts that have been flagged by the method for impending failure.

While specific apparatus and methods have been shown by way of example embodiments herein, it should be understood that other and different embodiments are possible. It is intended that the disclosure is to cover all modifications, equivalents, and alternatives falling within the scope of the claims.

What is claimed is:

1. A method of predicting failures of an in vitro diagnostic instrument, comprising:
   monitoring, via one or more monitoring devices associated with one or more components of the in vitro diagnostic instrument, two or more condition-based maintenance (CBM) parameters of the in vitro diagnostic instrument;
   providing the two or more condition-based maintenance parameters of the in vitro diagnostic instrument to a local database of a local data server storing data on the functionality and condition-based maintenance parameters of the one or more components of the in vitro diagnostic instrument in memory in the local database;
   transmitting the condition-based maintenance data to a remote server which is a CBM analysis server; wherein:
      the transmitting of the condition-based maintenance data to the remote server comprises a conditional push operation where a condition is required to be met before the transmitting takes place;
   storing the condition-based maintenance data at the CBM analysis server;
   generating predictions via the CBM analysis server of impending failures of components of the in vitro diagnostic instrument based on failure prediction criteria, wherein a pattern of the condition-based maintenance data is compared against known patterns in a failure pattern library of the CBM analysis server for that component, wherein the comparison comprises threshold-based comparisons, wherein if a preselected threshold is exceeded, then a failure is predicted to occur;
   assigning a confidence level via the CBM analysis server to a generated prediction of impending failure of a component of the in vitro diagnostic instrument, the confidence level based on a degree of deviation from the preselected threshold; and
   initiating a suitable action by the CBM analysis server if the deviation from the failure prediction criteria is above a defined threshold amount;
   wherein the two or more condition-based maintenance parameters of the in vitro diagnostic instrument comprise a software-related CBM parameter of component connectivity and one or more of:
      a temperature of a component of the in vitro diagnostic instrument;
      a pressure in a component of the in vitro diagnostic instrument;
      a liquid level in a component of the in vitro diagnostic instrument;
      a current drawn by a component of the in vitro diagnostic instrument;
      a flow rate through a component of the in vitro diagnostic instrument; and
      a backlash in a pump component of the in vitro diagnostic instrument.

2. The method of claim 1, comprising processing the two or more condition-based maintenance parameters to provide processed condition-based maintenance data, wherein the processed condition-based maintenance data comprises a maximum, minimum, mean, and standard deviation of the two or more condition-based maintenance parameters over a predefined period of time.

3. The method of claim 1, comprising setting a collection frequency of the two or more condition-based maintenance parameters of the in vitro diagnostic instrument.

4. The method of claim 1, comprising setting an upload frequency of the condition-based maintenance data of the in vitro diagnostic instrument.

5. The method of claim 1, wherein the transmitting of the condition-based maintenance data to the remote server further comprises a pull operation where the transmitting is requested by the remote server.

6. The method of claim 1, wherein generating predictions of impending failures of components of the in vitro diagnostic instrument by the CBM analysis server comprises determining a failure pattern match, wherein the failure pattern match comprises exceeding a predetermined slope of the condition-based maintenance data over a predetermined period of time.

7. The method of claim 1, wherein the action comprises triggering one or more predefined rules from the CBM analysis server, wherein the predefined rules comprise one or more of:
   provide a notice or warning to an instrument operator;
   create a report;

9 request more condition-based maintenance data from the instrument;

automatic instrument shutdown; and schedule service of the instrument.

8. The method of claim 1, wherein the condition required to be met before the transmitting takes place is based on preprogrammed intervals.

9. The method of claim 1, wherein the suitable action includes ordering replacement of parts predicted to fail.

10. An in vitro diagnostic instrument maintenance apparatus, comprising:

one or more monitoring devices configured to monitor condition-based parameters of one or more instrument components of one or more instruments;

a local server coupled to the one or more monitoring devices, the local data server configured to:

test functionality of the one or more instrument components, and obtain the condition-based parameters of the one or more instrument components;

a local database configured to contain a compilation of the condition-based parameters; and a remote server configured to communicate with the local data server and configured to receive and store the condition-based parameters in a condition-based maintenance (CBM) parameter database, the remote server including a memory comprising:

the CBM parameter database, a failure pattern library, and a rules database, wherein:

the condition-based parameters comprise software-related operating parameters including component connectivity and one or more of:

a temperature of a component of the in vitro diagnostic instrument;

a pressure in a component of the in vitro diagnostic instrument;

10 a liquid level in a component of the in vitro diagnostic instrument;

a current drawn by a component of the in vitro diagnostic instrument;

a flow rate through a component of the in vitro diagnostic instrument; and a backlash in a pump component of the in vitro diagnostic instrument; wherein:

the remote server compares condition-based parameters stored in the CBM parameter database against failure patterns and normal patterns stored in the failure pattern library; and the remote server, based on a rule collected from the rules database, initiates a suitable action if the condition-based parameters stored in the CBM parameter database are determined to be dissimilar enough from a normal pattern or similar enough compared to a failure pattern stored in the failure pattern library to indicate an impending failure of a component of an in vitro diagnostic instrument.

11. The in vitro diagnostic instrument maintenance apparatus of claim 10, wherein the local database is configured to receive the condition-based parameters from multiple in vitro diagnostic instruments.

12. The in vitro diagnostic instrument maintenance apparatus of claim 10, wherein the software-related operating parameters further comprise one or more of processor crash occurrences, processor restart occurrences, local server processor utilization, and memory usage.

13. The in vitro diagnostic instrument maintenance apparatus of claim 10, wherein the condition-based parameters of the one or more instrument components are processed to determine a rate of change over time or a difference over time.

14. The in vitro diagnostic instrument maintenance apparatus of claim 10, wherein the local data server is a local workstation server.

* * * * *